US011759128B2

(12) United States Patent
Raykhman et al.

(10) Patent No.: US 11,759,128 B2
(45) Date of Patent: **\*Sep. 19, 2023**

(54) METHOD AND APPARATUS FOR NON-INVASIVELY MONITORING ANALYTES IN DOMESTICATED ANIMALS

(71) Applicant: InESA, Inc., East Greenwich, RI (US)

(72) Inventors: Alexander M. Raykhman, East Greenwich, RI (US); Rodion Raykhman, Attleboro, MA (US)

(73) Assignee: INESA, INC., East Greenwich, RI (US)

( * ) Notice: Subject to any disclaimer, the term of this patent is extended or adjusted under 35 U.S.C. 154(b) by 267 days.

This patent is subject to a terminal disclaimer.

(21) Appl. No.: 16/919,964

(22) Filed: Jul. 16, 2020

(65) Prior Publication Data
US 2020/0337614 A1    Oct. 29, 2020

Related U.S. Application Data

(62) Division of application No. 15/092,592, filed on Apr. 6, 2016, now Pat. No. 10,716,497.

(60) Provisional application No. 62/143,285, filed on Apr. 6, 2015.

(51) Int. Cl.
*A61B 5/145*    (2006.01)
*A61B 5/00*    (2006.01)
*A61B 10/00*    (2006.01)

(52) U.S. Cl.
CPC ........... *A61B 5/14532* (2013.01); *A61B 5/68* (2013.01); *A61B 10/0051* (2013.01)

(58) Field of Classification Search
CPC ......... A61B 5/0205; A61B 5/68; A61B 5/682; A61B 5/6896; A61B 5/1455; A61B 5/14551; A61B 5/14552; A61B 5/14532; A61B 5/4277; A61B 5/1468; A61B 5/1473; A61B 5/1486
See application file for complete search history.

(56) References Cited

U.S. PATENT DOCUMENTS

| | | |
|---|---|---|
| 5,139,023 A | 8/1992 | Stanley |
| 5,941,821 A | 8/1999 | Chou |
| 6,067,941 A | 5/2000 | Axelrod |
| 7,386,333 B1 | 6/2008 | Birecki et al. |
| 7,635,331 B2 | 12/2009 | Kim et al. |
| 7,729,734 B2 | 6/2010 | Mandelis et al. |
| 2007/0283973 A1* | 12/2007 | Longley .................. A61F 5/566 131/329 |
| 2008/0247910 A1 | 10/2008 | Weekamp et al. |
| 2011/0054938 A1 | 3/2011 | Hood et al. |
| 2013/0289370 A1 | 10/2013 | Sun et al. |
| 2016/0157836 A1 | 6/2016 | Borg et al. |
| 2017/0296809 A1* | 10/2017 | Ruflin ................ A61N 1/36014 |

* cited by examiner

*Primary Examiner* — Chu Chuan Liu
(74) *Attorney, Agent, or Firm* — Burns & Levinson LLP; Jerry Cohen

(57) ABSTRACT

A device and method for noninvasively monitoring biofluids of an animal provides measuring physical parameters of an analyte with a device located within an oral cavity of the animal.

4 Claims, 4 Drawing Sheets

METHOD AND APPARATUS FOR NON-INVASIVELY MONITORING ANALYTES IN DOMESTICATED ANIMALS

CROSS REFERENCE TO RELATED APPLICATIONS

This application is a divisional of co-pending of U.S. application Ser. No. 15/092,592, filed Apr. 6, 2016, and entitled METHOD AND APPARATUS FOR NON-INVASIVELY MONITORING ANALYTES IN DOMESTICATED ANIMALS, which in turn claims priority to and the benefit of U.S. Provisional Application No. 62/143,285, filed Apr. 6, 2015, each of which are incorporated by referenced herein in their entirety for all purposes.

BACKGROUND

Millions of households throughout the world spend billions of dollars each year on their pets. The American Pet Product Manufacturers Association (APPMA) regularly conducts a National Pet Owners Survey. In its most recent survey for 2011-2012, the APPMA estimated that there were 377.41 million pets in the United States, with 164.6 million or 43.6% of them being cats (86.4M) or dogs (78.2M). The total spending on pets according to the survey was $50.96 billion and is expected to rise nearly two billion dollars when its next survey is conducted. Of that, $25.18 billion was spent on supplies, over the counter medicine and vet care. If we extrapolate those figure, roughly $10.98 billion of the $25.18 billion is spent on cats and dogs.

Dog diabetes is a relatively common dog health issue that all too often goes undetected until an emergency occurs. While only about 1 in 500 dogs are diagnosed, some estimates show that as many as 1 in 100 dogs have diabetes. This means that about 782,000 registered dogs required diabetic treatment in the US.

The above-presented numbers indicate that blood glucose monitoring for dogs and cats has a solid market-based foundation.

Until recently, there have not been any methods and/or devices specifically designed to provide accurate non-invasive measurements of the blood glucose level in domesticated animals including dogs and cats. Devices developed for monitoring the human blood glucose level have been used instead, with a slight modification of the peripheral members of the instruments and measurement procedures. From a technological point of view, all existing methods for the blood glucose spot measurement or blood glucose curve building are either invasive (clinic blood test, clinic or home test using electro-chemical blood measuring devices like One-Touch Ultra™—relatively accurate; accuracy is affected by stress) or inaccurate (urine test).

All known approaches related to domesticated animals require collecting certain amounts of some biological material, not necessarily a blood sample, e.g., urine, saliva or tear liquid. Regardless of the kind of biological material used, each of these substances can be obtained by sampling that suggests a human interaction with the animal. In particular, a sample collecting container should be physically removed from contacting the animal for further analysis of its content (U.S. Pat. No. 5,139,023). A very few methods and methods-corresponding technologies can be named for obtaining information about the blood glucose level in domesticated animals that hypothetically do not require sampling. These techniques may include measuring the tissue's electrical conductivity, compressibility and thermal diffusivity successfully applied in the GlucoTrack™ product of Integrity Applications, Inc., electromagnetic absorption constant (US Pat. Pub. No. 20130289370), absorption of laser/infrared radiation (U.S. Pat. No. 7,729,734), magneto-resonance absorption (U.S. Pat. No. 7,635,331), photo-acoustics (U.S. Pat. No. 5,941,821) and many others. All these measurement methods are complicated by practically overall hairiness of the most of domesticated animals.

In-clinic stress may cause blood glucose to be elevated making it difficult to determine the true blood glucose level In order to get the most accurate readings, blood glucose monitoring is best done under the pet's typical daily conditions. This is usually the home environment where feeding, exercise, and stress levels are normal. Blood glucose values obtained in the clinic often do not accurately reflect the values of a typical day, complicating the regulation process.

The purpose of the present invention is presenting a method and at least one conceptual design of an apparatus for accurate non-invasive measurement of the domesticated animal's blood glucose level causing no stress to the animal oblivious to the fact that the measurement is being conducted.

BRIEF SUMMARY

The foregoing and other problems are overcome by methods and devices in accordance with embodiments of this disclosure, wherein a specially-shaped biofluids collector is combined with a sensory network to obtain information about an analyte (e.g., blood glucose) level in domesticated animals by camouflaging the collector as an animal's toy. The device provides for a stress-free, non-invasive measurement of the analyte and automatically controls the measurement process based on signals from sensors responsible for identifying that the biofluid collector is positioned in the designated space inside the animal's oral cavity. Measurements are allowed only upon confirmation that the biofluids collector is positioned correctly inside the oral cavity of the animal. Different biological elements are used by sensors to gather information about the blood glucose level, thereby allowing use of sophisticated data mining analytical technique including neural networking and genetic algorithms.

In one embodiment a method and device for measuring at least one analyte level in an animal is disclosed, wherein the device may comprise a body having a predetermined shape and size at least partially insertable into an oral cavity of the animal so as to expose a surface of the body to biofluids in the oral cavity, and an analyte measuring system housed with the body. The analyte measuring system may include a biosensing unit for measuring at least one analyte in biofluids present in the oral cavity of the animal, and a signal output component operably coupled to the biosensor and configured to generate at least one output signal in response to activation of the biosensing unit.

In another embodiment, the biosensing unit may be comprised of one or more sensors indicating a desired positioning of the body at least partially within the oral cavity of the animal. A computing means, such as a circuit or microprocessor, may activate the biosensing unit to acquire analyte sensing data only while the body is in the desire position in the oral cavity. For example, if the toy is dropped by the animal, measurements would be halted until the toy is properly repositioned in the animal's mouth.

In yet another embodiment, the biosensing unit may comprise a BFC, a means for transporting the biofluids (e.g., capillary conduits or pores in the toy surface, etc.) from the oral cavity to the BFC, and a sensory network comprised of a plurality of the sensors disposed around and/or within the BFC.

In another aspect, the biosensing unit may include a biofluid container (BFC), and one or more capillary conduits connected on a first end to the BFC and having a second end positioned at, or near, the surface of the chew toy so as to permit biofluids to be collected and transported from the animal's oral cavity to the BFC. One or more sensors may be configured to be in fluid connection with the transported to and collected at the BFC. The sensors may be any type of sensor providing meaningful information regarding, for example, the volume of collected biofluid(s), or physical variables from which the position of the toy and/or the analyte concentrations may be determined. For example, the sensor(s) may detect a set of physical variables functionally dependent on glucose concentration in the biofluids, and in response output physical variable signals. From the physical variable signals, a computing unit that may be implemented as a circuit, processor, or other means, housed within the toy, or in remote wireless communication with biosensing unit, may determine the glucose level. Such sensors may include electrochemical sensors, photoelectric sensors, infrared sensors, acoustic sensors and electromagnetic sensors, etc. The computing unit may operate to condition the physical variable signals to provide stable data and to estimate variables for determining the at least one analyte level. The estimating variables may possess unambiguous relationship with the at least one analyte level, making them useful as components of a vector input of a biosensing unit calibration function. The computing unit may be configured to build the calibration function and calculate the analyte concentration in the biofluids. Those of skill in the art will readily appreciate that any of the aforementioned functions may be performed by a computing unit contained within the toy or remotely located, or divided between such computing units.

These and other aspects of this disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not a limitation of the invention. In addition, it should be appreciated that structural features shown or described in any one embodiment herein can be used in other embodiments as well.

Another embodiment of the present invention may provide a method for measuring at least one analyte level in biofluids of an animal, comprising the steps of: disposing an analyte collection and measurement device in proximity to an animal; determining when the analyte collection and measurement device is potentially exposed to biofluids of the animal while the animal is relaxed; collecting biofluids in response to the step of determining; measuring at least one analyte in collected biofluids of the animal with a biosensing unit; and generating an output signal in response to measurement by the biosensing unit.

The method may further comprise wirelessly transmitting the output signal from the analyte collection and measurement device. The step of determining may include sensing the presence of the analyte collection and measurement device within the oral cavity of the animal and sensing motion of the analyte collection and measurement device. The step of measuring comprises detecting a set of physical variables functionally dependent on glucose concentration in the bio fluids and computing from the step of detecting a glucose value in response to the physical variable signals. The step of computing may include creating estimating variables, building a calibration function and calculating values of an analyte concentration in the bio fluids.

BRIEF DESCRIPTION OF THE FIGURES

The illustrations of the accompanying drawings are not necessarily to scale, emphasis instead being placed upon illustrating the principles of the examples, wherein.

DETAILED DESCRIPTION

Figure 1:
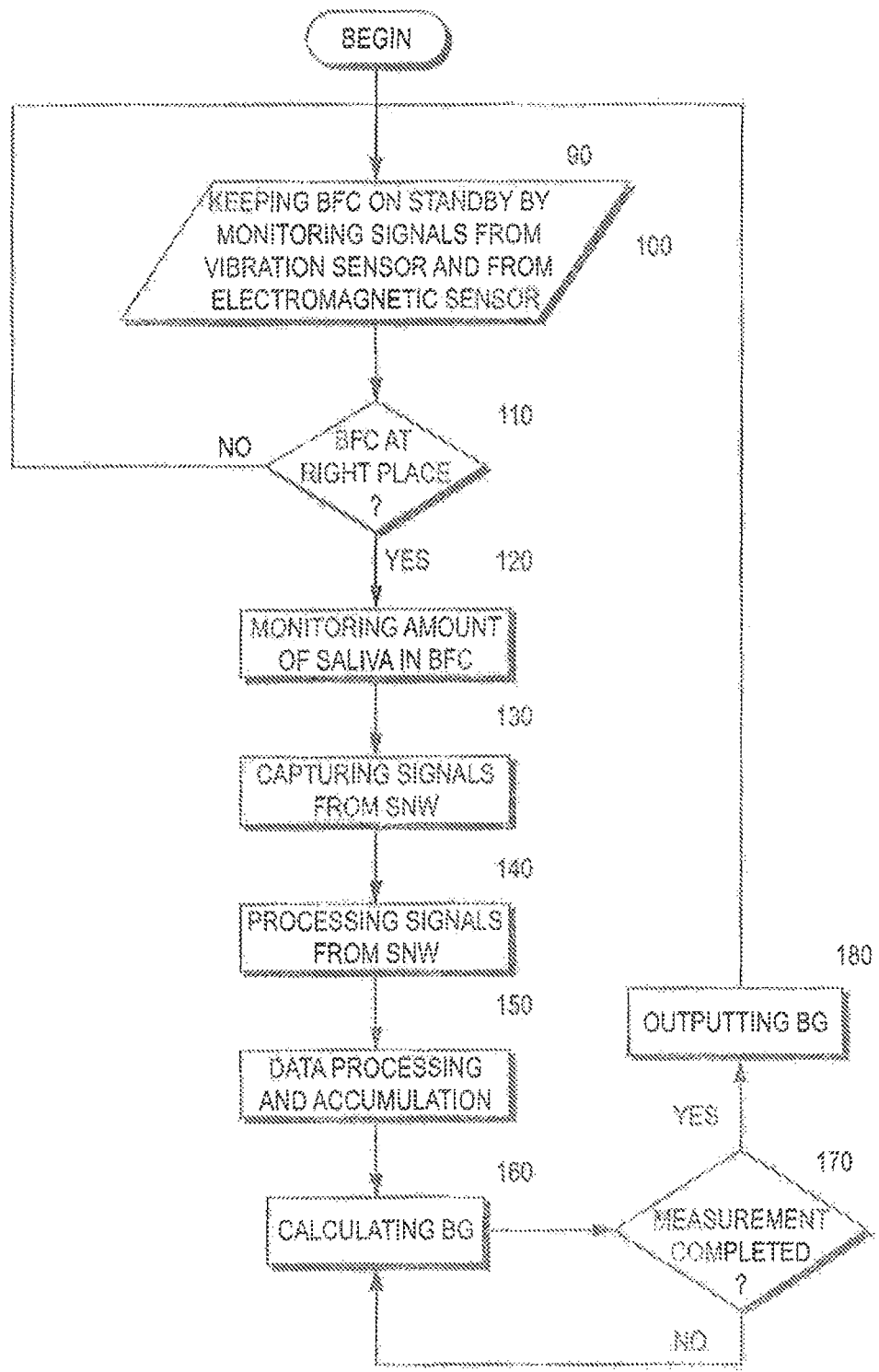
FIG. 1 is a flow chart of a method in in accordance with an exemplary embodiment of the invention.

Reference is now made to the figures, depicting implementations of methods and devices for measuring an analyte, such as blood glucose level, in domesticated animals. In the detailed descriptions of embodiments that follow, glucose is measured through use of a bone-shaped toy housing 10 for an analyte measuring system 12 sensing the animal's biofluid 14 (i.e., saliva.) However, the descriptions are in no way intended to limit the scope of the invention to that particular analyte or biofluid (e.g., other biofluids could include mucus, blood, breath, etc.), or to the specific configurations of components described. A bone shaped toy housing 10 assists in properly positioning the sensing portion of the analyte measuring system 12 properly in the animal's oral cavity 16, but other shapes conceivably also accomplish this goal. Similarly, the signal output device 18 in a described embodiment comprises a wireless transmitter for transmitting sensed physical variables and/or computed analyte levels to a remote receiver 20, however those of skill in the art would readily appreciate alternative analyte readout mechanisms, such as an output port on the device that may be connected and disconnected to a remote computing system.

The presented novel solution to measuring blood glucose level in domesticated animals is based on the following operating principles and/or components:

1. A specially-designed BFC 22 capable of accumulating the biofluids 14 without being noticed by the animal;
2. a multi-channel sensory network 24 for simultaneous measurement of a set of physical variables functionally-dependent on the glucose concentration in the biofluid 14;
3. at least two of the glucose-relating physical variables demonstrate orthogonally toward environmental disturbances to the process of measurement;
4. at least two of the glucose-relating physical variables are captured by interacting with at least two different body's biological elements;
5. wireless control of the measurement process and measured data outputting; and
6. self or forced cleaning of the biological fluid collector when the measurement system is idle.

The first principle ensures an accurate measurement of the blood glucose level by eliminating the development of the so-called "stress sugar" during the sample taking.

The second and the third principles provide for an effective application of methods of regression analysis and optimization and artificial intelligence (neural networking, genetic algorithms, etc.) for designing an optimal measurement algorithm The fifth and the sixth principles support the non-invasive and undistinguishable nature of the proposed blood glucose measurement which is crucially important once the measurement is applied to animals.

With reference to FIG. 1, a measurement process 90 may include a sequence of the following steps that will be described below in detail.

The process 90 begins at step 100, where the analyte measuring system 12 is on standby and receiving signals indicating positioning of the toy from one or more continuously sensing sensors, such as a vibration signal from a vibration sensor 30 and for an electromagnetic signal from a measurement coil 32. Both the vibration sensor 30 and the measurement coil 32 may be incorporated in the body of the analyte measuring system 12.

In step 110, the analyte measuring system 12 may be activated, initiating the measuring procedure, when the vibration signal coupled with the electromagnetic signal indicate that the BFC 22 is positioned in the predetermined zone in the animal's oral cavity 16. While proper positioning is not detected, continuous monitoring of the sensor 30, 32 continues but no analyte-level related sensor measurement data is acquired. As noted above, correct positioning of the BFC 22 may be assured by the special bone-like shape of the toy housing 10. When the animal clinches to the toy 10 inside the oral cavity 16, it creates a specific spectral response that can be captured by a vibration sensor 30, e.g., accelerometer (such as described on the www.ultimompd.com website, although unrelated to the glucose measurement). Then, the vibration signal may decay, indicating the fact that the toy 10 is not moving. At the same time, an electromagnetic sensor, by measuring the impedance of the hard pallet in a certain frequency range, may indicate that the toy 10 is positioned within the limits of a distance between the center of mass of the toy 10 and the animal's hard pallet. Together, these two signals may identify the moment when the toy 10 is in the position suitable for the measurement. Additionally or alternative, a plurality of pressure sensors (not shown) may be used also, disposed about the circumference of the toy 10 and spread along a certain length on the toy 10.

In step 120, monitoring may be activated based on the amount of the saliva 14 in the BFC 22 by using signals relating to the amount of accumulated saliva, as determined from one or more sensors 34. The amount of saliva may be used to trigger the measuring processing. Data collection by the sensory network 24 will depend on a sufficient amount of biofluid 14 (i.e., saliva) is accumulated. An animal may take and drop the toy 10 as many times as it wants without affecting the quality of the measurement. There are a variety of methods for measuring volume or mass of liquid material in the BFC 22 that may be used. For example, optical (transparency of the medium is evaluated), ultrasound ("Time of flight" paradigm can be used, or wave's phase shift captured at the sides of the container) capacitance-based methods, floating level sensors, and many more.

In step 130, signal capture is initiated from each sensor 34 of the sensory network 24 located inside and or in the vicinity the BFC 22. The signals capturing sequence may be controlled by the amount of saliva required for each member of the sensory network 24 to generate responses satisfying the requirements of the high quality signal processing.

In step 140, signals are processed from the sensory network 24.

In step 150, a vector is sent of glucose-sensitive signals obtained from the sensory network 24 a data processing module 36 for data processing and storage, generation of the estimating variables further used by a mathematical procedure for outputting the desired value of the glucose concentration in the animal's biofluid 14

In step 160, the analyte (i.e., blood glucose, etc.) level may be calculated from the measured signals.

Figure 4:
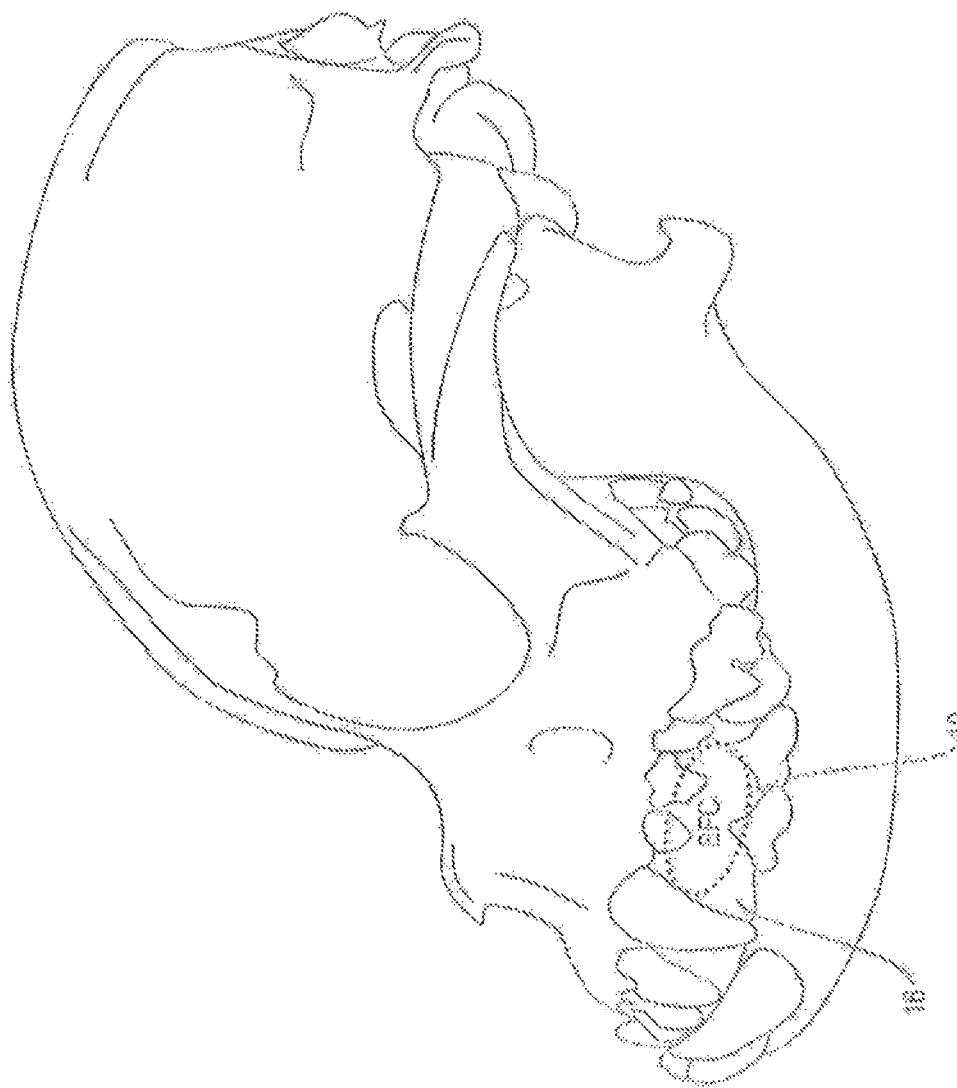
FIG. 4 is an illustration of an analyte measuring device in a possible desired position within a dog's oral cavity.

In step 170, a determination is made whether sufficient data has been collected to complete the measurement and determine the analyte level. If not, the measuring and calculating continue. If the measurement has completed, the analyte level may be output (step 180) and the process returns to the determination at step 110 whether additional analyte-level related sensor 24 data acquisition may proceed. If the animal drops the toy 10, or otherwise misplaces the BFC 22 from the desired position (e.g., position 40 in FIG. 4) in the oral cavity 16, the measuring process is interrupted, and the data acquired to that point is stored for aggregation with future acquired data once the conditions of step 110 are satisfied.

In step 180, the measuring process may be completed and "measurement completed" confirmation signals collected from each measuring information channel of the analyte measuring system 12, and the resulting measured value(s) of the blood glucose output to recipients.

Figure 2:
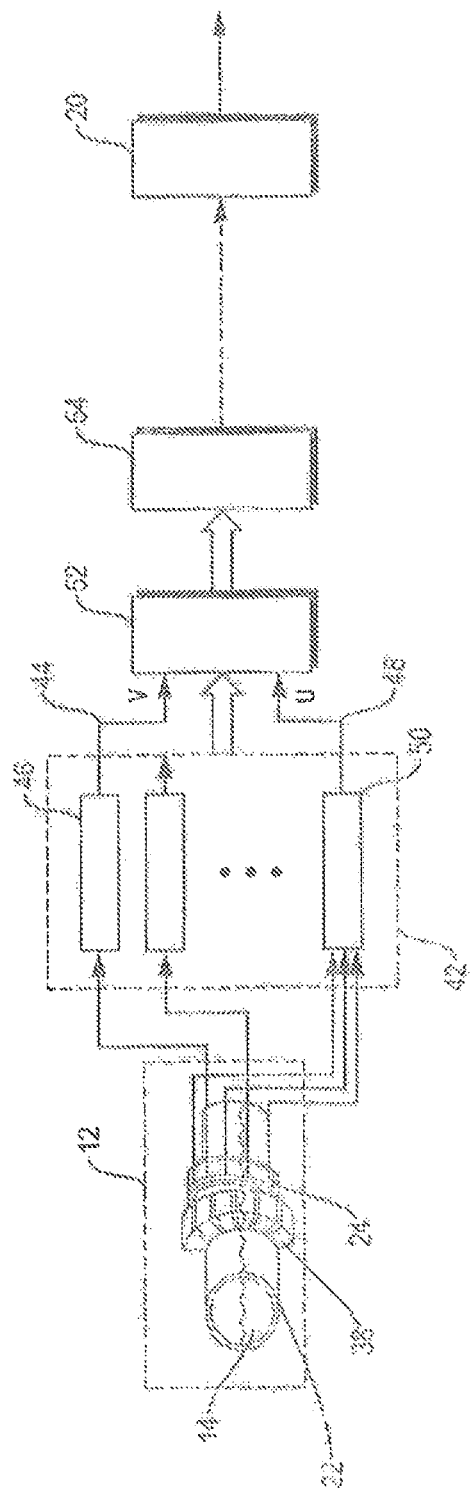
FIG. 2 is an illustration of an exemplary functional block diagram of an analyte measuring device.

A functional block-diagram of an embodiment of the analyte measuring system 12 and toy housing 10 facilitating the above-described measurement process is shown in FIG. 2. According to this diagram, the BFC 22 (shown with its housing removed for clarity) collects saliva 14 via a system or systems of capillary-type conduits 38. Saliva 14 is accumulated in a fluids sample container 40. One or more sensors of the sensory network 24 may be arranged around or inside the same BFC 22. The sensors in each sensory network 24 could be based on proven glucose measuring technologies, such as disclosed in U.S. Pat. Nos. 6,954,462, 6,882,940, 6,405,069, 6,377,828 and 6,309,352, the contents of each of which are hereby incorporated by reference. The sensors of sensory network 24 provides responses of the highest possible accuracy and precision because the sampled saliva is being accumulated in the BFC 22 under the absence of disturbing factors that usually accompany measurements performed on living organisms. This near laboratory degree of accuracy and precision of measurements is a substantial advantage of the present method and apparatus. Regardless of which physical property of the tissue or body fluid is measured in order to monitor the glucose concentration in a living mammal organism, having this specimen isolated from disturbing factors produced or experienced by a normally functioning organism, improves the accuracy and precision of measurements and creates an opportunity for a simultaneous use of a variety of sensors which responses link the glucose concentration to measurable physical properties of the fluid, e.g., dielectric constant, compressibility, thermal diffusivity, and electromagnetic absorption constant, etc. The vector of signals from the sensory network 24 may be sent to a signal conditioning computing unit 42, where each component of the vector is treated in accordance with the particular properties of the sensor generating the respective signal(s).

The conditioned signal (v) 44 from a vibration sensor 46 and a conditioned signal (u) 48 from an electromagnetic sensor 50, the each delivering information about the position and the positional stability of the toy 10 in the animal's oral cavity 16, are used in accordance with the measurement method for automatically controlling the method's sequence of operations. Additionally, the electromagnetic sensor 50 may be used for measuring the blood glucose level by evaluating the complex impedance of the electromagnetic coupling between the measuring coil and the tissue of the animal's hard palate.

Finally, the conditioned vector-output of the sensory network 24 may go to a generator of estimating variables 52, which is shown as a distinct functional block but which could be a function performed by computing unit 42 or a remote computing system. This functional block takes the conditioned signal or signals from some group of sensors and converts then into a variable that carries information about the glucose level and allows its further conversion into the glucose concentration by a blood glucose concentration calculator block 54 (which also could be implemented within computing unit 42, or at a remote computing system.) The output of the blood glucose concentration calculator block 54 may be wirelessly transferred to receiver 20, where an additional mathematical analysis of the gathered blood glucose level readings can be performed.

Various implementations of the proposed system are possible with different functional roles playing by the apparatus' analog and digital hardware within the logic of the proposed algorithm and functional block diagram of the apparatus. For example, the estimating variables can be generated within the sensory network 24 and the glucose concentration in blood can be calculated after the vector of estimating variables has been wirelessly transferred to a remote blood glucose calculator.

Figure 3:
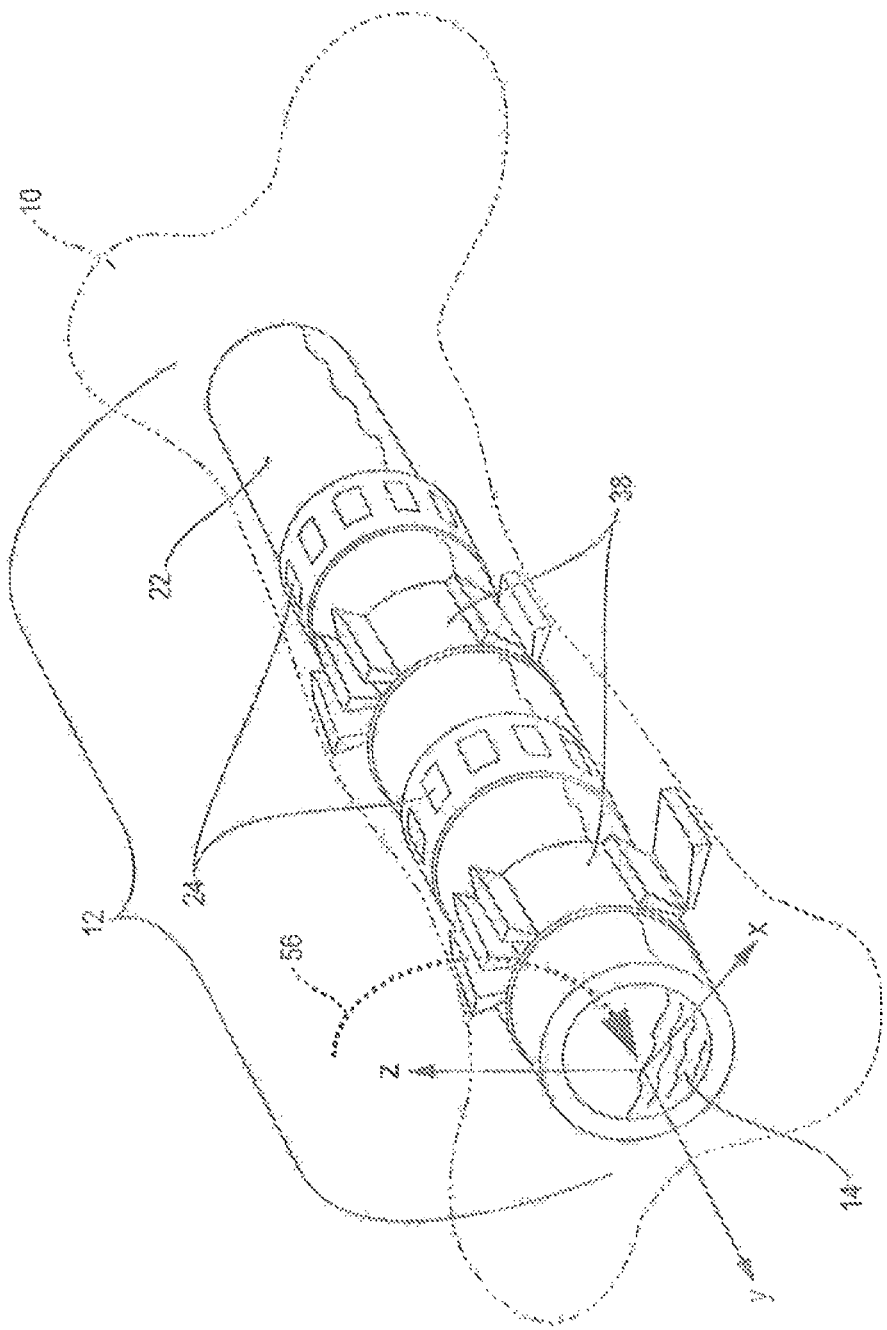
FIG. 3 is a schematic illustration of a chew toy embodiment of an analyte measuring device in accordance with the invention.

A schematic illustration of the bone-shaped toy housing 10 and an analyte measuring system 12 is shown with greater detail in FIG. 3. In this embodiment, analyte measuring system 12 is comprised of the registries of capillary-type conduits 38 for capturing and directing the biofluids 14 into the BFC 22 as indicated by arrow 56. The capillary-type conduits 38 and the sensory network 24 are assembled around the BFC 22 so the measurements are possible at any angular position of the BFC 22 rotating around the axis "y" in a coordinate system xyz shown. As an example of the invention application to measuring the blood glucose level in dogs, the outline of the BFC toy housing 10 resembles a bone which curves provide for guiding the BFC 22 into a designated position in the oral cavity 16 of the particular dog. An illustration of the conceptual idea of how the BFC 22 is self-positioned in the dog's oral cavity 16 is given in FIG. 4. When an animal, e.g., a dog, plays with the bone-looking toy 10, the animal will not notice that the measurement will be conducted each time when the "bone" will be taken by the animal into the animal's mouth and automatically positions itself inside the mouth at the designated place. The plurality of sensors capturing different physical variables from different biological substances of the animal creates a sufficient vector of informative variables that substantiate accurate measurement of the animal blood glucose concentration in real time.

Based on the provided description of the measurement's algorithm and the apparatus implementing the measurement method, one can build a device for the accurate, non-invasive blood glucose level measurement in domesticated animals without causing any stress to the animal that is the main source of error in all the existing measurement methods.

As used above, the terms "comprise," "include," and/or plural forms of each are open ended and include the listed parts and can include additional parts that are not listed. "And/or" is open ended and includes one or more of the listed parts and combinations of the listed parts. "Terms" and "coefficients" have been used interchangeably in the description above.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A method for measuring at least one analyte level in biofluids of an animal, comprising the steps of:
    disposing a body of an analyte collection and measurement device in an oral cavity of the animal, wherein the body has a predetermined shape and size at least partially insertable into the oral cavity of the animal and configured to expose a surface of the body to biofluids in the oral cavity;
    determining when the analyte collection and measurement device is potentially exposed to biofluids of the animal by sensing the presence of the analyte collection and measurement device within the oral cavity of the animal and sensing the motion of the analyte collection and measurement device;
    collecting biofluids in response to the step of determining;
    measuring at least one analyte in collected biofluids of the animal with a biosensing unit; and
    generating an output signal in response to measurement by the biosensing unit, wherein the analyte collection and measurement device comprises: the body of the analyte collection and measurement device;
    an analyte measuring system housed within the body, including
    the biosensing unit for measuring at least one analyte in biofluids present on the surface of the body in the oral cavity of the animal, comprising:
    at least one capillary conduit connected on a first end to a biofluid container and a second end disposed at or near the surface of the body and configured to enable collection and transport of biofluids from the oral cavity of the animal to the biofluid container, and
    at least one analyte sensor in fluid connection with biofluids transported to the biofluid container; and
    a signal output component operably coupled to the biosensing unit and configured to generate the output signal in response to the at least one analyte sensor.

2. The method of claim 1, further comprising wirelessly transmitting the output signal from the analyte collection and measurement device.

3. The method of claim 1, wherein the step of measuring comprises detecting a set of physical variables functionally dependent on analyte concentration in the biofluids and computing from the step of detecting an analyte concentration value in response to the physical variable signals.

4. The method of claim 3, wherein the step of computing includes creating estimating variables, building a calibration function and calculating values of the analyte concentration in the biofluids.

\* \* \* \* \*